United States Patent
Chen et al.

(10) Patent No.: US 9,649,347 B2
(45) Date of Patent: May 16, 2017

(54) **PROTECTIVE EFFECTS AND APPLICATION OF A *LACTOBACILLUS RHAMNOSUS* ON THE ALLEVIATION OF CHRONIC ALCOHOLIC LIVER INJURY**

(71) Applicant: Jiangnan University, Wuxi (CN)

(72) Inventors: Wei Chen, Wuxi (CN); Fengwei Tian, Wuxi (CN); Wenli Huang, Wuxi (CN); Jianxin Zhao, Wuxi (CN); Hao Zhang, Wuxi (CN); Gang Wang, Wuxi (CN); Qiuxiang Zhang, Wuxi (CN); Xiaoming Liu, Wuxi (CN); Daming Fan, Wuxi (CN); Feifei Chi, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 14/980,606

(22) Filed: Dec. 28, 2015

(65) Prior Publication Data

US 2016/0113975 A1  Apr. 28, 2016

Related U.S. Application Data

(63) Continuation-in-part of application No. 14/117,833, filed on Nov. 15, 2013, now abandoned.

(51) Int. Cl.
| | | |
|---|---|---|
| *A01N 63/02* | (2006.01) |
| *A61K 35/747* | (2015.01) |
| *C12R 1/225* | (2006.01) |
| *A23C 9/123* | (2006.01) |
| *C12N 1/20* | (2006.01) |
| *A23L 33/135* | (2016.01) |

(52) U.S. Cl.
CPC .......... *A61K 35/747* (2013.01); *A23C 9/1234* (2013.01); *A23L 33/135* (2016.08); *C12N 1/20* (2013.01); *C12R 1/225* (2013.01); *A23Y 2220/73* (2013.01)

(58) Field of Classification Search
None
See application file for complete search history.

(56) References Cited

U.S. PATENT DOCUMENTS

| | | | | |
|---|---|---|---|---|
| 8,389,266 B2 * | 3/2013 | Tsuboi | ................. | A23C 9/1234 424/439 |
| 8,697,054 B2 * | 4/2014 | Chambaud | ........... | A23C 9/1234 424/93.45 |

* cited by examiner

*Primary Examiner* — Vera Afremova

(74) *Attorney, Agent, or Firm* — CBM Patent Consulting, LLC

(57) ABSTRACT

An anti-oxidative *Lactobacillus rhamnosus* CCFM1107 can relieve chronic alcoholic liver injury, and *L. rhamnosus* CCFM1107 can be used in preparing dairy products as starter culture. The dairy products of this invention include milk, milk powder, milk capsules or fermented milk containing *L. rhamnosus* CCFM1107. It has strong abilities of anti-oxidation, scavenging diphenyl picrylhydrazyl (DPPH) radical and hydroxyl radical, inhibiting lipid peroxidation, tolerating cholate, chlorine sodium and pH, and can improve liver function and antioxidative index, lower serum endotoxin level and regulate intestinal flora distribution, thus effectively relieving alcoholic liver injury of mice.

5 Claims, 5 Drawing Sheets

PROTECTIVE EFFECTS AND APPLICATION OF A *LACTOBACILLUS RHAMNOSUS* ON THE ALLEVIATION OF CHRONIC ALCOHOLIC LIVER INJURY

This application is a continuation-in-part application of U.S. patent application Ser. No. 14/117,833 filed Nov. 15, 2013 that is a national stage of international application Ser. No. PCT/CN2012/078861 which claimed the priority to the Chinese patent application CN 201210046322.0 filed on Feb. 28, 2012.

FIELD OF INVENTION

The present invention relates to the field of microbial technology. More particularly, it relates to a *Lactobacillus rhamnosus* which can relieve chronic alcoholic liver injury, and also to the use of said *Lactobacillus rhamnosus*.

BACKGROUND OF THE INVENTION

Alcohol abuse and alcohol dependence have become increasingly serious public health problems in the world today. There is an increasing trend of alcoholic liver injury in China, so alcohol has become the second pathogenic cause of liver injury following viral infection. Alcohol-induced liver injury mainly includes alcoholic fatty liver, alcoholic hepatitis, alcoholic liver fibrosis and alcoholic cirrhosis. Alcoholic liver injury can also lead to other diseases and conditions such as the problem that blood cannot be filtered thoroughly by liver, hyperlipidemia, cardiovascular and cerebrovascular diseases, lower liver catabolism, diabetes, gallstones, kidney disease, acute fatty liver of pregnancy and damage to the digestive system. Therefore, it is important to investigate the pathogenesis of alcoholic liver diseases and seek for prevention and therapy measures against alcoholic liver injury.

It is believed that the alcoholic liver injury mainly results from toxic metabolites of ethanol metabolism in the liver cells and the subsequent metabolic disorders. The specific reasons of alcoholic liver injury include: 1. toxic effects of acetaldehyde: acetaldehyde interacts with cysteine, glutathione and vitamin E to promote lipid peroxidation; acetaldehyde combines with multiple proteins of liver as antigens to stimulate the body to produce antibodies, causing corresponding immune response and resulting in the damage to liver cells; and acetaldehyde can also combine with important functional groups of enzymes, resulting in the changes of enzyme activities, thereby affecting the enzyme function. 2. Adverse effects of free radicals: A large amount of free radicals and reactive oxygen species can be produced during ethanol metabolism; these free radicals not only can damage the liver cells directly, but also increase the susceptibility of liver cells to lipid peroxidation, thus causing liver cell damage. 3. Induction of endotoxin: ethanol intake disturbs intestinal microflora and destroys the integrity of structure and function of the intestinal mucosa at the same time, so as to increase the permeability of intestinal mucosa. Therefore the endotoxin level in blood is increased to produce a plurality of cytokines, among which inflammatory cytokines cause liver cell injury. At present, the main treatments for alcoholic liver injury include abstinence, nutritional therapy, drug therapy, gene therapy, and therapies for alcoholic liver disease-related diseases. The most commonly used method is drug treatment, which has certain effects but many deficiencies. For example, many drugs may promote more blood lipids to be metabolized in the liver, which promotes lipid accumulation in the liver and cause liver function damage. The metabolism of these drugs in liver may possibly increase the liver burden further; some drugs take effect slowly, and even cause drug resistance and side effects. Therefore, researchers are actively developing new treatments and intervention strategies for alcoholic liver diseases. Probiotics without drug resistance and side effects have been widely used to improve human health, especially directed for prevention and treatment of alcoholic liver diseases (FIG. 5), gradually causing public concern.

Probiotics are living microorganisms that have beneficial effects on the host when administered in adequate amounts. The said probiotics include *Lactobacillus, Bifidobacterium* and some *Streptococcus* strains. Generally, they have special physiological effects and health functions such as regulating intestinal microflora of the host, treating antibiotic-associated diarrhea, reducing blood cholesterol levels, inhibiting infection resulting from pathogenic bacteria such as *Escherichia coli, Helicobacter pylori* and so on. In addition, probiotics can effectively eliminate free radicals to promote antioxidative activity of the host, reduce the endotoxin level and regulate the immune system. These functions reveal that probiotics can play a role in relieving alcoholic liver injury. However, it has been rarely reported that probiotics have hepato-protective effects. Therefore, it is significant to investigate the application of probiotics on the uses as health foods to relieve alcoholic liver injury. With increasing attention on alcoholic liver injury and wider uses of probiotics, the dietary intervention of probiotics and probiotic products on alcoholic liver diseases will have a very broad market prospects.

At present, the published patent applications for the prevention and treatment of alcoholic liver injury mainly focuses on Chinese medicine compositions. For example, CN101224232A discloses that flavones extracted from the root of radix puerariae can inhibit the increasing permeability of small intestine, reduce the blood alcohol concentration, decrease the alcohol absorption and relieve alcoholic liver damage. CN 101961367A discloses a Chinese medicine composition for prevention of alcoholic liver injury, composed of fungal polysaccharide and silybum marianum extract with good solubility, rapid disintegration in the gastrointestinal tract to enhance the immunity of the host and to function as an adjuvant to protect the liver from alcoholic injury. CN 102058632A and CN 102160637A also separately disclose the protective effects of herbs and their extracts on alcoholic liver injury. As for dairy products, such as CN 101623032A discloses a kind of milk that can help protect the host from alcoholic liver injury. Such milk added with soluble dietary fiber, lecithin, soybean peptide and so on can enhance liver function, accelerate alcohol metabolism and relieve alcoholic liver injury. CN 101328469A also discloses a *Streptococcus thermophilus* grx02 that protects the liver from alcoholic injury. However, these patents do not fully relate to a probiotic *Lactobacillus* that can regulate intestinal flora and relieve chronic alcoholic liver injury.

Therefore, it is necessary to search for probiotics and related foods and compositions that can regulate intestinal microflora and relieve chronic alcoholic liver injury.

DETAILED DESCRIPTION OF THE INVENTION

Technical Question to be Solved

One object of the present invention is to provide a *Lactobacillus rhamnosus* that has anti-oxidative properties and protective effects against chronic alcoholic liver injury.

Another object of the present invention is to provide the use of said *Lactobacillus rhamnosus* CCFM1107. The method of acquiring the strain of *Lactobacillus rhamnosus* CCFM1107 is also disclosed in this invention.

*Lactobacillus rhamnosus* CCFM1107 of present application was deposited on Nov. 29, 2011 under CGMCC Accession Number: 5496 in the China General Microbiological Culture Collection Center (CGMCC) having an office at Address: NO. 3, Yard 1, West Beichen Road, Chaoyang District, Beijing Institute of Microbiology, Chinese Academy of Sciences, Beijing100101, P. R. China (CN). CGMCC is an International Depository Authority. The deposit has been accepted by CGMCC under the provisions of Budapest Treaty and that all restrictions upon public access to the deposit material will be irrevocably removed upon the grant of a patent on this application.

CGMCC deposits are made under the provisions of the Budapest Treaty on the International recognition of the Deposit of Microorganism for the Purpose of Patent Procedure and the Regulations thereunder (Budapest Treaty). The treaty assures maintenance of viable cultures for 30 years from the date of deposit. The *Lactobacillus rhamnosus* CCFM1107 is available from CGMCC under the terms of the Budapest Treaty which assure permanent and unrestricted availability of progeny of the cell line to the public upon issuance of the pertinent U.S. patent application. The Budapest Treaty assures the availability of the cell line to one determined by U.S. Commissioner of Patents and Trademarks to be entitled thereto according to 35 U.S.C. §122 and the commissioner's rules pursuant thereto.

The assignee of the present application has agreed that if the cell line deposit should die, be lost or destroyed when cultivated under suitable conditions, it will be promptly replaced with viable specimen of the same cell line upon proper notification. Availability of a deposited cell line is not to be construed as a license to practice the invention in contravention of the rights granted under the authority of any government in accordance with its patent laws.

Technical Plan

The invention is achieved through the following technical solutions.

The present invention relates to an isolated *Lactobacillus rhamnosus* CCFM1107, deposited at the General Microbiology Culture Collection Center of China Committee for Culture Collection of Microorganisms under accession number CGMCC5496. The invention also relates to a dairy composition for relieving alcoholic liver injury, comprising the said *Lactobacillus rhamnosus* CCFM1107.

The invention also relates to a dairy composition which further comprises milk, milk powder, milk capsules or fermented milk.

The invention also relates to a dairy composition which contains at least $10^6$ CFU/ml *Lactobacillus rhamnosus* CCFM1107.

The invention also relates to a method for preparing the said dairy composition, which comprises: i) inoculating sterilized skim milk with the *Lactobacillus rhamnosus* CCFM1107 of claim 1, and incubating at 37° C. for 14-16 h, which forms as curd; ii) inoculating sterilized skim milk with the curd of step i, and incubating at 37° C. for 14-16 h, which results in curd; iii) inoculating sterilized skim milk with the curd of step ii, and incubating at 37° C. for 14-16 h, which forms curd that named as a mother starter; iv) inoculating sterilized skim milk with the mother starter, and incubating at 37° C. for 14-16 h, which forms curd as a starter culture which contains $1-3\times10^9$ CFU/ml bacteria; v) mixing the starter culture with a sterilized raw milk which contains at least $10^6$ CFU/ml *Lactobacillus rhamnosus* CCFM1107, and storing at a refrigerator.

According to a preferable embodiment of the invention, the method for preparing the said dairy composition comprises: i) inoculating MRS liquid medium with 1-5% of the *Lactobacillus rhamnosus* CCFM1107 of claim 1 by weight, and incubating at 37° C. for 12-16 h; ii) inoculating MRS liquid medium with 1-5% of the mixture of step i by weight, and incubating at 37° C. for 12-16 h; iii) inoculating MRS liquid medium with 2-4% the mixture of step ii by volume, and incubating at 37° C. for 16-18 h, collecting cell pellets by centrifuge; iv) suspending the cell pellets in the sterilized skim milk at the concentration of $1-3\times10^9$ CFU/ml bacteria which results in a starter culture; v) mixing the starter culture with a sterilized raw milk which contains at least $10^6$ CFU/ml *Lactobacillus rhamnosus* CCFM1107, and storing at a refrigerator.

According to a preferable embodiment of the invention, the method for preparing the said dairy composition further comprises: i) mixing the raw milk with the starter culture of claim 5, incubating at 37° C. for 12-18 h which yields fermented milk; ii) mixing the fermented milk and the sterilized raw milk, homogenizing, vacuum-concentrating and spray-drying which yields milk powders which are optionally capsulated as milk capsules.

According to a preferable embodiment of the invention, the raw milk is one or more kinds of milk selected from skim milk, fresh milk, or reconstituted milk wherein the milk is selected from cow's milk, goat's milk or mare's milk.

According to a preferable embodiment of the invention, the method for preparing the said dairy composition further comprises: i) adding 3-5% of the starter culture according to claim 5 and 3-5% of commercial culture by volume into the sterilized raw milk; ii) homogenizing, fermenting at 37° C. until the concentration of lactic acid is up 0.6-0.7%; iii) cooling and storing in a refrigerator.

According to a preferable embodiment of the invention, the commercial culture contains *Lactobacillus bulgaricus* or/and *Streptococcus thermophilus*.

The present invention in more details will be described.

The present invention relates to a *Lactobacillus rhamnosus* CCFM1107, deposited at the General Microbiology Culture Collection Center of China Committee for Culture Collection of Microorganisms on Nov. 29, 2011 under accession number CGMCC5496.

The inventor selected a probiotic CCFM1107 from the strains isolated and preserved in the laboratory and identified the probiotic CCFM1107 as *Lactobacillus rhamnosus* CCFM1107 by microbiological characteristics such as morphological and cultural characteristics, and molecular identification method based on 16S rDNA sequence. The bacterial strain was deposited in the General Microbiology Culture Collection Center of China Committee for Culture Collection of Microorganisms on Nov. 29, 2011 under accession number CGMCC5496.

The said *Lactobacillus rhamnosus* CCFM1107 has the following morphological characteristics:

Colony characteristics: transparent, milky white, round, pigment-free colonies in MRS agar with neat edge, smooth wet surface and the diameter between 0.5-1.0 mm. Refer to FIG. 1.

Bacterial characteristics: gram-positive, rod-like cells, single, in pair or in chain, nonsporeforming, round at both ends. Refer to FIG. 2.

The *Lactobacillus rhamnosus* CCFM1107 of the invention has the following culture characteristics:

The *Lactobacillus rhamnosus* CCFM1107 of this invention has a relatively short lag phase. It enters into the logarithmic phase at 4 h, reaches the stable phase at 14 h-16 h and gradually declines after 24 hours, and the cell number begins to decrease.

The *Lactobacillus rhamnosus* CCFM1107 of this invention has the following characteristics in liquid culture:

The *Lactobacillus rhamnosus* CCFM1107 grows well in MRS liquid medium. The bacterial culture medium becomes turbid after approximate four-hour incubation. Bacterial cells begins to precipitate after cultured for about 8 h, no bubble is generated with gentle shake, bacterial pellets begin to appear after cultured for 12 h, and the milky bacterial pellets increase significantly after cultured for 20 h. The bacterial cells firmly attach to the bottom of the culture medium with clear supernatant, and the pH value fell from 6.2 to 3.8.

In the present invention, the said MRS liquid medium is the *Lactobacillus* medium sold by BD Difco Company with the trade name Bacto® lactobacilli MRS Broth, which is well known to those skilled technicians in the field. It may also be the same commercial culture media produced by relevant domestic companies.

The *Lactobacillus rhamnosus* CCFM1107 of this invention can be used in a traditional fermented food. It is classified as Generally Recognized As Safe (GRAS) strain according to the list of edible microbial strain published by Chinese Ministry of Health and can be used in fermented foods.

This invention also relates to the use of said *Lactobacillus rhamnosus* CCFM1107 in preparing dairy composition as starter culture.

The said *Lactobacillus rhamnosus* CCFM1107 starter culture is prepared as follows:

Generally, the pure culture of *Lactobacillus rhamnosus* CCFM1107 should be inoculated repeatedly to restore the strain viability. A small amount of the pure culture is inoculated in skim milk which is sterilized at 110° C. for 10 min, and cultured at 37° C. The strain and skim milk are oscillated slowly for the first few hours until thoroughly mixed; and then they are on standing until solidification. After solidification, the solidified culture of 1-2 mL is absorbed from the bottom with a sterile pipette, and added to the sterilized skim milk aseptically. The strains can be sufficiently activated after the steps are repeated several times to prepare the mother starter culture.

Then, the *Lactobacillus rhamnosus* CCFM1107 strains are inoculated in skim milk by 12% weight of skim milk which is sterilized at 110° C. for 10 min, and then incubated into curd at 37° C. for 14-16 h. The curd is cultured and activated for two subsequent generations at the same conditions to obtain the fermented skim milk as mother starter;

The said pasteurization is performed with a sterilization machine such as 145 C from the UK SPX APV company.

The skim milk is a dairy product well-known for those in the field. The raw milk is tested, filtered, preheated to about 38° C., and centrifuged with a closed separator from Sweden Alfa-Laval to obtain cream and skim milk. So the said skim milk can be obtained by this method.

The said mother starter culture is inoculated in the skim milk by 3-5% volume of skim milk which is sterilized at 110° C. for 10 min, and then incubated at 37° C. for 14-16 h to obtain the starter culture with the viable bacteria concentration of $1-3\times10^9$ cfu/mL.

The quality of starter culture directly affects the quality of fermented dairy products. Therefore, sensory examinations shall be conducted to determine its uniform solidification, smoothness, densification, elasticity, sour taste and aroma, smell and bubbles; and chemical examinations are also necessary to determine its acidity. The titration acidity is generally 90-110° T; for the conventional methods in the technical art, see GB 4789.2-2010 Determination of Total Bacteria Count, National Food Safety Standards, the Ministry of Health of the PRC. The viable bacteria concentration of *Lactobacillus rhamnosus* CCFM1107 should reach $1-3\times10^9$ cfu/mL.

Or, the said *Lactobacillus rhamnosus* CCFM1107 starter culture is prepared according to the following steps:

The *Lactobacillus rhamnosus* CCFM1107 strain is inoculated in MRS liquid medium by 1-5% weight of MRS liquid medium and incubated at 37° C. for 12-16 h, and activated for two subsequent generations at the same condition. The activated culture by volume of 2-4% MRS liquid medium is inoculated in the MRS liquid medium at 37° C. for 16-18 h, and then centrifuged at the speed of 4000 r/min at 4° C. for 15 min to obtain the cell sediments after removing supernatant. The cell sediments are suspended with sterilized skim milk to obtain the starter culture with the viable bacteria concentration of $1-3\times10^9$ cfu/mL.

The dairy composition of this invention comprises the milk, milk powder, milk capsule or fermented milk containing said *Lactobacillus rhamnosus* CCFM1107.

According to this invention, the milk containing said *Lactobacillus rhamnosus* CCFM1107 is prepared by the following steps:

Raw milk is sterilized at 95° C. for 20 min or at high temperature of 140° C. for 2 s, cooled to 4° C., then added with the *Lactobacillus rhamnosus* CCFM1107 bulk culture with the concentration over $10^6$ cfu/mL, and stored at 4° C. to obtain the milk containing *Lactobacillus rhamnosus* CCFM1107.

In this invention, the heating and sterilizing devices are those commonly used in the field and commercially available. The said thermal sterilization is performed with a sterilization machine such as 145 C type sold by SPX APV company, UK.

The said high temperature sterilization is performed with a tube and plate type UHT such as PT-20C-R from Japanese Powerpoint International, Ltd.

The milk containing the *Lactobacillus rhamnosus* CCFM1107 can be added with excipients that are commonly used in the field, such as granulated sugar, stabilizer, flavor, food colors, fruit juice and so on.

The said raw milk is one or more kinds of milk selected from skim milk, fresh milk and reconstituted milk; and the said milk is cow milk, goat milk or mare milk. For example, the skim milk is skim cow milk, skim goat milk or skim mare milk; the fresh milk is fresh cow milk, fresh goat milk or fresh mare milk. The reconstituted milk should be considered as raw milk blended with concentrated whole milk and/or whole milk powder, and water.

According to this invention, the milk powder or milk capsule containing the said *Lactobacillus rhamnosus* CCFM1107 is prepared by the following steps:

Raw milk is sterilized at 95° C. for 20 min or at high temperature of 140° C. for 2 s to obtain the sterilized raw milk; the sterilized raw milk is cooled to 37° C., inoculated with the *Lactobacillus rhamnosus* CCFM1107 starter culture by 4% volume of raw milk, fermented at 37° C. for 16 h to obtain the fermented milk containing *Lactobacillus rhamnosus* CCFM1107; the fermented milk containing *Lac-* tobacillus rhamnosus CCFM1107 is added to the sterilized raw milk by the volume ratio of 1:3, and then homogenized, vacuum-concentrated and spray-dried to obtain the milk powder containing Lactobacillus rhamnosus CCFM1107.

The said homogenization is a technology that is commonly used in food production. The homogenization in food processing refers to that the material liquid is extruded, shocked and expanded with loss of pressure so that the material is refined and mixed more evenly. For example, fat globules in milk are broken into small ones with a homogenizer for more stable products in the dairy processing. The homogenization is often carried out with a homogenizer which is the important processing device in the food and dairy processing field. The homogenizer used in the invention is commercially available in the field of art, such as the high-pressure homogenizer GYB40-10S sold by Shanghai Donghua high-pressure homogenizer Factory.

According to this invention, the vacuum concentration is the technology that is often used in food production. There are no difficulties for those skilled technicians in the field to choose the concentration temperature and the vacuum degree according to material properties. The vacuum concentration apparatuses used in the invention are commercially available, such as the vacuum evaporator sold by Yangzhou Food Machinery Factory.

According to this invention, the spray drying is the technology that is often used in food production. There is no difficulty for those skilled technicians in the field of art in choosing the drying temperature and the drying time according to material properties. The spray drying apparatuses used in the invention are commercially available, such as the experimental spray dryer sold by Shanghai Triowin Technology Company Limited.

According to this invention, the said milk powder containing the Lactobacillus rhamnosus CCFM1107 is loaded into capsules to obtain the capsule product.

According to this invention, the said capsules are pharmaceutical and food products sold on the market.

According to this invention, the said fermented milk containing the Lactobacillus rhamnosus CCFM1107 is prepared by the following steps.

Raw milk is sterilized at 95° C. for 20 min or at high temperature of 140° C. for 2 s to obtain the sterile raw milk, thus obtained sterile raw milk is cooled to 37° C., added with the Lactobacillus rhamnosus CCFM1107 starter culture by 3-5% volume of raw milk and commercial starter culture which can prepare fermented milk by 3-5% volume of raw milk, fermented at 37° C. to 0.6-0.7% titration acidity (by lactic acid) after mixing, cooled to 4° C. and stored under refrigerating temperature to obtain the fermented milk containing said Lactobacillus rhamnosus CCFM1107.

The said commercial culture is Lactobacillus bulgaricus and Streptococcus thermophilus, such as the products of Danisco or Chr Hansen.

Lactobacillus bulgaricus is widely used in the manufacturing process of fermented milk, which is classified under Lactobacillus Genera. It is named as Lactobacillus delbrueckii subsp bulgaricus (Lactobacillus bulgaricus for short) by microbiologists for its origin, microbiological characteristics, and excellent performance and so on.

Streptococcus thermophilus is an important starter culture bacterium for fermented milk, widely used in the production of fermented dairy products, including yogurt and cheese. Streptococcus thermophilus also has some functional activities, such as producing extracellular polysaccharide, bacteriocin and vitamin.

The Method of Acquiring the Strain CCFM1107 by Ultraviolet Mutagenesis

The inventor selected a probiotic CCFM1107 from the strains isolated and preserved in the laboratory by using a ultra-violet mutagenesis method for bacterial strain improvement. Strain CCFM1107 was acquired based on its acid tolerance and anti-oxidation capabilities via the following ultra-violet mutagenesis method.

Acid tolerance is an important evaluation standard on beneficial probiotic lactic acid bacteria. In vitro anti-oxidation capability is also an important index to evaluate the anti-oxidation capability of specific probiotic. The original strain CCFM0528 shows an obviously weaker acid tolerance and in vitro anti-oxidation capabilities. Therefore, we use an ultraviolet mutagenesis strategy to improve the acid tolerance and in vitro anti-oxidation capabilities of the original strain CCFM0528. The following is the ultraviolet mutagenesis protocol for strain improvement. Microbial culture of original strain CCFM0528 after three successive subculture was inoculated into liquid MRS culture media with a 2% (w/w) inoculation rate, and then incubated to the midanaphase of logarithmic growth under 37° C. to form the optimum physiological state. Ten milliliter bacterial culture was centrifuged for 10 minutes under a speed of 6000 r/min. Then the supernatant was discarded to collect the bacterial cells. The bacterial cell pellet was then washed three times by phosphate buffer solution (PBS, pH 7.2) and re-suspended in PBS. And the bacterial cell concentration was adjusted to $10^8$ CFU/mL. And fine glass beads were added to the suspension solution, the suspension was thoroughly mixed on a votex mixer to break apart cells in cluster and then filtered through sterile absorbent cotton to form single cell suspension.

Five milliliters of the above-prepared bacterial cell suspension were added to a sterile 9 cm petri dish containing a stir bar, and then put on a magnetic stirrer, and placed under a 15 w ultraviolet lamp with a 30 cm distance to the lamp. The bacterial cell suspension was then ultraviolet-radiated for 0, 15, 30, 45, 60, 75, 90 seconds, respectively, while the suspension was magnetically stirred for even exposure. The ultraviolet-treated cell suspension was spread on the MRS plate and after a 48-hour incubation 363 potentially mutated colonies were formed.

Then we inoculated the potentially mutated colony in liquid MRS culture media and incubate them for 24 hours under 37° C. Then the well-grown bacterial culture was inoculated in the liquid MRS media with a pH 3.5 with a 2% (w/w) inoculation rate, and incubated for 24 hours under 37° C., and the optical density ($OD_{600nm}$) was determined by a spectrophotometer. With the original strain as a control, the relative growth rates (R) of different mutated strains were calculated as the following equation. The bigger the relative growth rates are, the higher acid tolerance the mutated strains have. The acid tolerance of one mutated colony was remarkably improved with a 35% increase of relative growth rates among 363 tested strains. We named this strain CCFM1107.

$$R = \frac{D - B - C}{A - B - C} \times 100\%$$

In this equation:
A: the optical density ($OD_{600nm}$) of the tested strain after 24-hour incubation in pH 6.5 MRS B: the optical density ($OD_{600nm}$) of the blank liquid MRS culture media C: the optical density ($OD_{600nm}$) of initial culture after inoculation D: the optical density ($OD_{600nm}$) of the tested strain after 24-hour incubation in pH 3.5 MRS The DPPH free radical scavenging capability of mutated strains was determined according to the method described by Lin et al (Lin M Y, Chang F J. Antioxidative effect of intestinal bacteria Bifidobacterium longum ATCC 15708 and Lactobacillus acidophilus ATCC 4356 [J]. Dig Dis Sci, 2000, 45(8): 1617-22). As showed in the following graph, compared to the original strain CCFM0528, the mutated CCFM1107 strain has the highest DPPH free radical scavenging rate.

Based on the above results, the inventors acquired an ultraviolet-mutated strain CCFM1107 of improved acid tolerance and DPPH free radical scavenging capabilities by using an ultraviolet mutagenesis method for strain improvement.

The inventors identified the probiotic CCFM1107 as Lactobacillus rhamnosus CCFM1107 by microbiological characteristics such as morphological and cultural characteristics, and molecular identification method based on 16S rDNA sequence. The bacterial strain was deposited in the General Microbiology Culture Collection Center of China Committee for Culture Collection of Microorganisms on Nov. 29, 2011 under accession number CGMCC5496.

Beneficial Effects

Lactobacillus rhamnosus CCFM1107 of this invention has a high antioxidative capacity; the intact cell and cell-free extracts of Lactobacillus rhamnosus CCFM1107 with the cell concentration of $10^{10}$ cfu/mL have the rates of scavenging diphenyl picrylhydrazyl (DPPH) radicals of 93.51% and 89.66% respectively; while the original CCFM0528 strain only has much lower rates of scavenging diphenyl picrylhydrazyl (DPPH) radical, with 58.43% for $10^{10}$ cfu/mL intact cell concentration, and 53.11% for $10^{10}$ cfu/mL cell-free extracts. The intact cell and cell-free extracts of Lactobacillus rhamnosus CCFM1107 with the cell concentration of $10^{10}$ cfu/mL have the rates of scavenging hydroxyl radicals of 94.16% and 93.87% respectively.

The intact cell and cell-free extracts of Lactobacillus rhamnosus CCFM1107 have certain reducing capacities. The intact cell and cell-free extracts with the cell concentration of $10^{10}$ cfu/mL have the reducing capacities equivalent to 392.07 µmol/L and 373.91 µmol/L cysteine hydrochloride. The Lactobacillus rhamnosus CCFM1107 also has the capability of inhibiting lipid peroxidation. The intact cell and cell-free extracts with the cell concentration of $10^{10}$ cfu/mL have the inhibition rates of lipid peroxidation up to 84.52% and 81.18%. The Lactobacillus rhamnosus CCFM1107 can tolerate the bile salt of 0.35%, sodium chloride of 8% and pH 3.0.

The animal experiments show that Lactobacillus rhamnosus CCFM1107 of the invention can improve liver function and antioxidative index, relieve endotoxemia and regulate intestinal flora distribution, thus effectively relieving alcoholic liver injury of mice. Its effect is similar to or even better than sunflower liver-aid tablets (Chinese herbs preparation) sold by Heilongjiang Sunflower Pharmaceutical Co., Ltd.

The Lactobacillus rhamnosus CCFM1107 strain was deposited in the General Microbiology Culture Collection Center of China Committee for Culture Collection of Microorganisms on Nov. 29, 2011 under accession number CGMCC5496.

SPECIFIC EMBODIMENTS

This invention will be better understood by the following embodiments. The apparatuses and measurement methods in these embodiments are those mentioned in this description, which are not repeated here.

Example 1

Identification of Lactobacillus rhamnosus CCFM1107 of this Invention Based on 16S rDNA Sequence The Lactobacillus rhamnosus CCFM1107 is inoculated in MRS medium and cultured at 37° C. for 18 h. The bacterial culture of 1 ml is performed according to the instructions of bacterial genomic DNA extraction kit. The genomic DNA is used as a template, the universal primers published in the literature (Critical evaluation of two primers commonly used for amplification of bacterial 16S rRNA genes. Applied and Environmental Microbiology, 2008, 74(8): 2461-2470), are used as the primers, PCR amplification is carried out in a 50 µL reaction system. The PCR products are purified, recovered and sequenced.

The PCR products were sequenced by Sangon Biotech (Shanghai) Co., Ltd. The sequencing results were compared to the NCBI nucleotide database to obtain the final result: CCFM1107 of this invention shows the homology up to 99% with Lactobacillus rhamnosus strain HT2, Lactobacillus rhamnosus strain 20300, and Lactobacillus rhamnosus NM94-5. Therefore, the CCFM1107 strain is identified as Lactobacillus rhamnosus strain. It was then deposited in the China General Microbiological Culture Collection Center on Nov. 29, 2011 under accession number CGMCC5496.

Example 2

Determination of the Microbiological Properties of Lactobacillus rhamnosus CCFM1107

Lactobacillus rhamnosus CCFM1107 is inoculated in the MRS medium by 5% (v/v), the pH value is determined at 0 h, 1 h, 2 h, 3 h, 4 h, 6 h, 8 h, 10 h, 12 h, 14 h, 16 h, 18 h, 20 h, 22 h and 24 h respectively, and the $OD_{600}$ value at 600 nm is measured. In this invention, the pH meter is from Mettler-Toledo Instruments (Shanghai) Co., Ltd. (320-S), and the spectrophotometer is UV-2100 Model UV-visible spectrophotometer manufactured by Unico (Shanghai) Instrument Co., Ltd.

Figure 1:
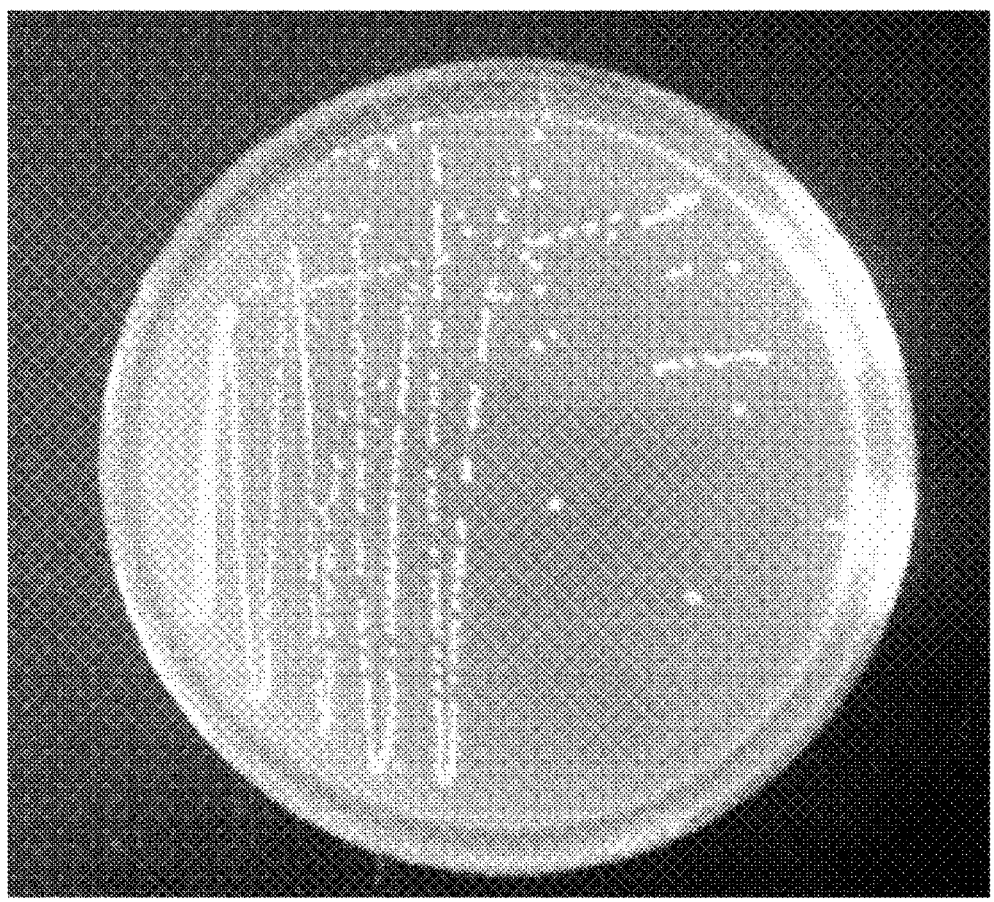
FIG. 1 shows the colony morphology of Lactobacillus rhamnosus CCFM1107.
Figure 2:
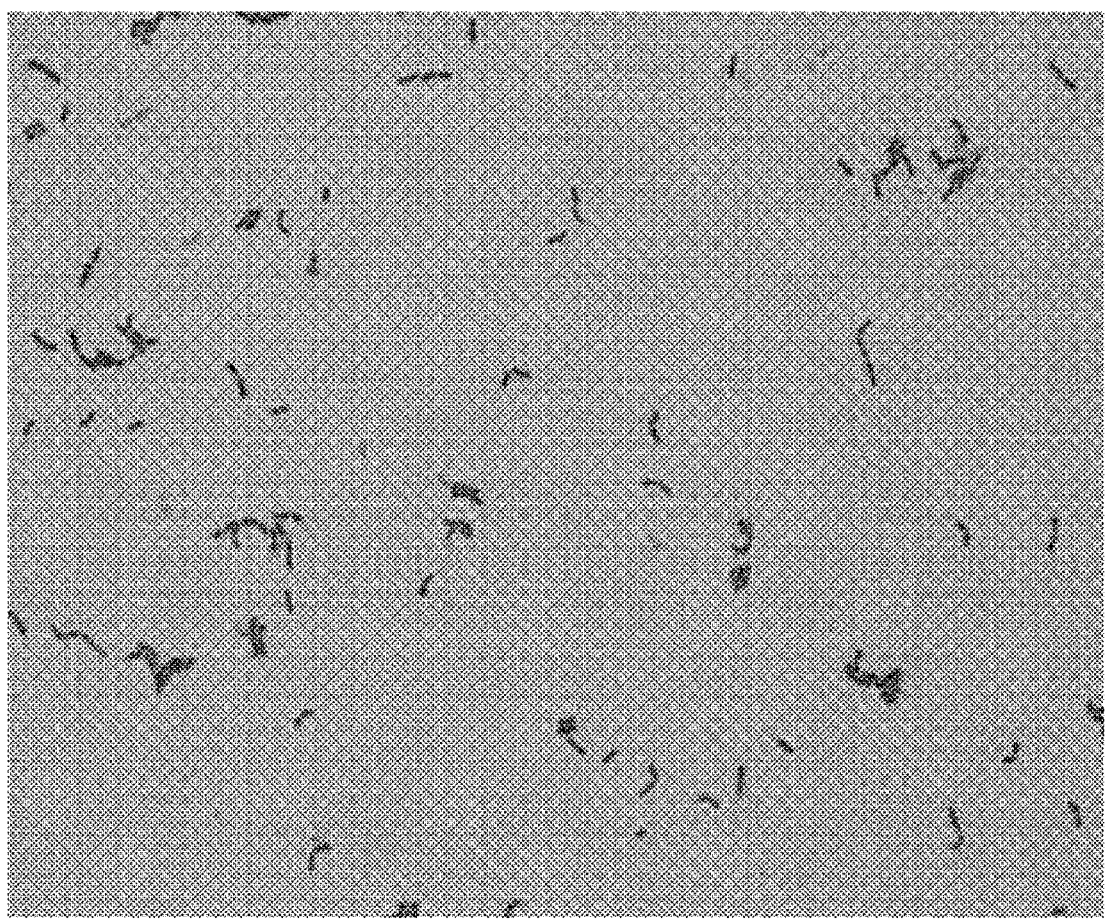
FIG. 2 shows the gram-stained bacterial morphology of Lactobacillus rhamnosus CCFM1107 (1000×)
Figure 3:
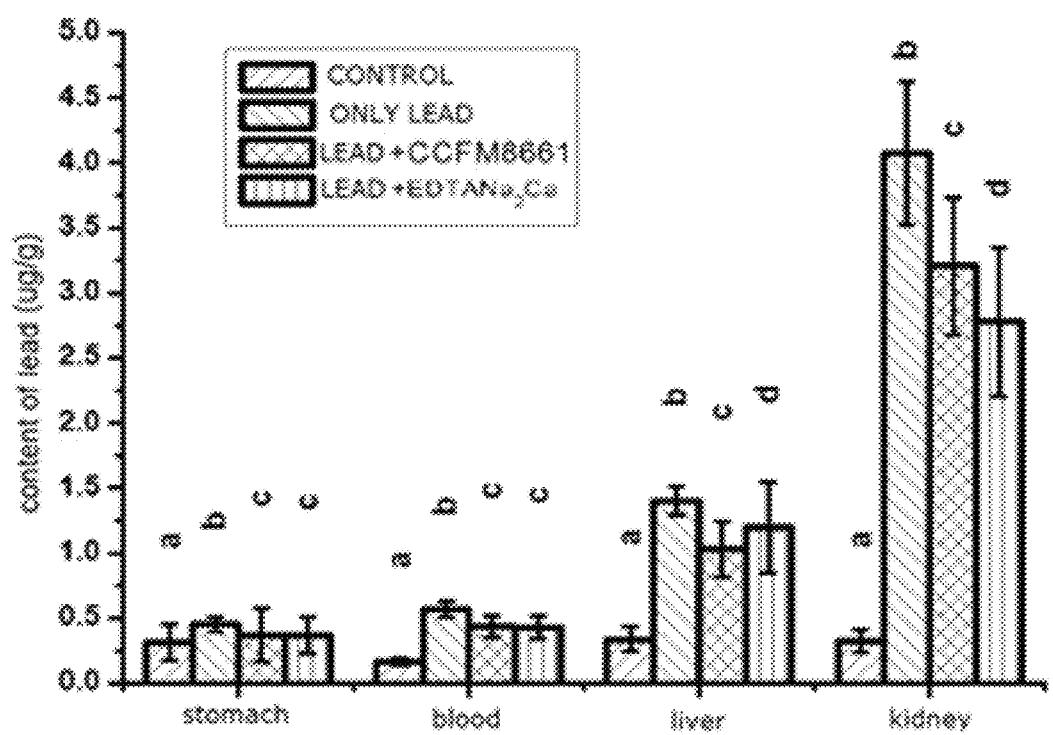
FIG. 3 shows the growth curve of Lactobacillus rhamnosus CCFM1107 cultured in MRS liquid medium at 37° C. under anaerobic conditions.

The $OD_{600}$ value and pH value can be mapped against incubation time to obtain the growth curve of *Lactobacillus rhamnosus* CCFM1107 in MRS medium, which is shown in FIG. 3. In the MRS medium, *Lactobacillus rhamnosus* CCFM1107 has a relatively short lag phase, then enters the logarithmic growth phase at 4 h and reaches the stable phase at 14-16 h. The pH value continues to drop with the incubation time. At the stable phase, the pH value keeps unchanged. pH drops from 6.13 to 3.86 after incubation for 24 h. The concentration of live *Lactobacillus rhamnosus* CCFM1107 is $6.8 \times 10^8$ cfu/mL.

Example 3

Anti-Oxidative Capacities of *Lactobacillus rhamnosus* CCFM1107

Firstly, the intact and cell-free extracts of *Lactobacillus rhamnosus* CCFM1107 are prepared.

*Lactobacillus rhamnosus* CCFM1107 of this invention is inoculated in MRS medium after activated, cultured at 37° C. for 24 h, and centrifuged at 6000 r/min for 10 min at 4° C. to obtain the culture supernatant and bacteria pellets. The bacterial pellets are washed twice with sterilized saline and re-suspended in sterilized saline to adjust the cell concentration to $10^9$ cfu/m L.

The obtained cell suspension is divided into two groups, namely intact cells (IC) and cell-free extract (CFE). The cell suspension is ultrasonically broken with a sonicator (Sonics & Materials Company, VCX500) at 4° C. by 200 W. The treatment is carried out for 5 s at an interval of 5 s, which lasts for 30 min. The cells are examined under a microscope to ensure there are not intact bacteria, and then centrifuged at 6000 r/min for 10 min at 4° C. to collect the supernatant, i.e. the cell-free extract.

Then the anti-oxidative capacities of *Lactobacillus rhamnosus* CCFM1107 are determined, including the radical-scavenging rate of DPPH and hydroxyl radical, the reducing activity and the inhibition rate of lipid peroxidation. These results are shown in Table 1.

(1) The Rate of Scavenging DPPH Radicals

DPPH (1,1-diphenyl-2-picrylhydrazyl radical) radical is a common and effective material for antioxidant screening and evaluation. It is a stable organic free radicals and purple in alcohol solution with a single electron, which has strong absorption at 517 nm. If substances capable of scavenging DPPH radicals are added, its absorption will be weakened, which can be used to determine the anti-oxidative properties of substances. The improved methods by MEEI-YN LIN and FEN-JUAN CHANG are used in this embodiment to calculate the rate of scavenging DPPH radicals of intact cell and cell-free extracts according to the calculation method given in the literature (Antioxidative effect of intestinal bacteria *Bifidobacterium longum* ATCC 15708 and *Lactobacillus acidophilus* ATCC 4356. Digestive Diseases and Sciences, 2000, 45(8):1617-1622).

(2) The Rate of Scavenging Hydroxyl Radicals

The hydroxyl radical is one of free radicals with the strongest reactivity and oxidizing capacity. It has strong abilities of binding DNA, proteins and lipids, so it's the main factor to cause oxidative damage in vivo. In this embodiment, Fenton reaction produces hydroxyl radicals HO., and o-phenanthroline-$Fe^{2+}$ is used as the redox indicator. With the HO. scavenger, there is less HO and more $Fe^{2+}$ and the solution turns red. The hydroxyl radical scavenging capability is expressed by the hydroxyl radical scavenging rate, which is calculated according to the calculation method given in the literature (The increased effectiveness of hydroxyl-radical scavengers in the presence of EDTA. Biochemical Journal, 1987, 243:709-714.).

(3) Determination of Reducing Activity

The reducing activity mainly refers to the capability of reducing oxygen free radicals and chelating $Fe^{2+}$ of some enzymes (e.g., catalase, NADH oxidase, NADH peroxidase) and non-enzyme complex (vitamin C, vitamin E, glutathione), thereby reducing oxidation reactions. The improved methods by Meei-Yn Lin and Chyuan-Liang Yen are used in this embodiment to calculate the reducing activity of intact cell and cell-free extracts. The reducing activity is expressed by the reducing capability, equivalent to the concentration of cysteine hydrochloride, which is calculated according to the calculation method given in the literature (Antioxidative ability of lactic acid bacteria. Journal of Agricultural and Food Chemistry, 1999, 47:1460-1466).

(4) Inhibition of Lipid Peroxidation

The lipid peroxidation mainly refers to a series of free radical reactions in presence of unsaturated fatty acids in the biomembrane. The final product of lipid peroxidation includes malondialdehyde (MDA), which can damage proteins, nucleic acids and other biological macromolecules, resulting in aging and a variety of diseases. The improved methods by MEEI-YN LIN and FEN-JUAN CHANG are used in this embodiment to calculate the inhibition rate of lipid peroxidation of intact cell and cell-free extracts. The capacity of inhibiting lipid peroxidation is expressed by the inhibition rate of lipid peroxidation, which is calculated according to the calculation method given in the literature (Reactive oxygen species and lipid peroxidation product-scavenging ability of yogurt organisms. Journal of Dairy Science, 1999, 82:1629-1634).

The rate of scavenging DPPH radical and hydroxyl radical, the reducing activity and the rate of inhibiting lipid peroxidation of intact cell and cell-free extracts are displayed in Table 1.

TABLE 1

Anti-oxidative capacities of *Lactobacillus rhamnosus* CCFM1107 (Compared to original CCFM0528 strain)

| Anti-oxidative index | DPPH scavenging rate/% | hydroxyl scavenging rate/% | Reducing activity/equivalent to concentration of cysteine hydrochloride (μmol/L) | The inhibition rate of lipid peroxidation/% |
|---|---|---|---|---|
| CCFM1107 Intact cell | 93.51 ± 3.57 | 94.16 ± 5.64 | 392.07 ± 7.15 | 84.52 ± 3.69 |

TABLE 1-continued

Anti-oxidative capacities of *Lactobacillus rhamnosus* CCFM1107 (Compared to original CCFM0528 strain)

| Anti-oxidative index | DPPH scavenging rate/% | hydroxyl scavenging rate/% | Reducing activity/equivalent to concentration of cysteine hydrochloride (μmol/L) | The inhibition rate of lipid peroxidation/% |
|---|---|---|---|---|
| CCFM0528 Intact cell | 58.43 ± 1.26 | 48.33 ± 3.2 | 145.76 ± 3.61 | 53.28 ± 3.82 |
| CCFM1107 Cell-free extract | 89.66 ± 4.02 | 93.87 ± 2.38 | 373.91 ± 6.36 | 81.18 ± 4.85 |
| CCFM0528 Cell-free extract | 53.11 ± 4.15 | 49.47 ± 3.5 | 163.46 ± 4.21 | 48.69 ± 4.35 |

From Table 1, the *Lactobacillus rhamnosus* CCFM1107 shows high activities in scavenging radicals and inhibiting lipid peroxidation, and the reducing activity. In conclusion, CCFM1107 has a relative high anti-oxidative activity among the selected bacteria strains.

Example 4

Tolerance Test of *Lactobacillus rhamnosus* CCFM1107 to Bile Salt

Bovine bile salt is added to the MRS medium at the final concentration of 0.0%, 0.10%, 0.20%, 0.30%, 0.35%, 0.40% and 0.45% (m/v) respectively. After sterilization, the *Lactobacillus rhamnosus* CCFM1107 of this invention is inoculated in the prepared bile salt-containing MRS medium by 5% (v/v). The growth of all groups is observed and the $OD_{600}$ value is measured after incubation at 37° C. for 24 h. The growth of *Lactobacillus rhamnosus* CCFM1107 is shown in Table 2 below. It is known that the inhibition effect of bile salts on bacteria depends on the bile salt concentration and the strains characteristics. The bile salt concentration in human intestine is 0.03%-0.30%, and only those strains that can grow and metabolize in the bile salts of normal physiological concentration can survive in the intestine. As shown in Table 2 the *Lactobacillus rhamnosus* CCFM1107 of this invention can grow in the medium at the bile salt concentration up to 0.35%. Therefore the *Lactobacillus rhamnosus* CCFM1107 has a strong tolerance to bile salts.

TABLE 2

The growth of *Lactobacillus rhamnosus* CCFM1107 in bile salts of different concentrations

| Bile salt concentration (%) | Growth |
|---|---|
| 0.00 | ++ |
| 0.10 | ++ |
| 0.20 | + |
| 0.30 | + |
| 0.35 | + |
| 0.40 | − |
| 0.45 | − |

Note:
++ indicates good growth, which means the medium is very turbid with visible bacterial pellets.
+ indicates a little growth, which means the medium is slightly turbid with a few visible bacterial pellets.
− indicates no growth, which means the medium is transparent without bacterial pellets.

Example 5

Tolerance Test of *Lactobacillus rhamnosus* CCFM1107 to NaCl

NaCl is added to the MRS medium at the final concentration of 0%, 2%, 4%, 6%, 7%, 8% and 9% (m/v) respectively. After sterilization, the *Lactobacillus rhamnosus* CCFM1107 of this invention inoculated in the MRS medium by 5% (v/v). The growth of all groups is observed and the $OD_{600}$ value is measured after incubation at 37° C. for 24 h. The results are shown in Table 3 below. It shows the *Lactobacillus rhamnosus* CCFM1107 of this invention can grow well in 7% NaCl, grow slowly in 8% NaCl and doesn't grow in 9% NaCl, which indicates that CCFM1107 can tolerate 8% NaCl.

TABLE 3

The growth of *Lactobacillus rhamnosus* CCFM1107 in NaCl of different concentrations

| NaCl (%) | Growth |
|---|---|
| 0 | ++ |
| 2 | ++ |
| 4 | ++ |
| 6 | ++ |
| 7 | ++ |
| 8 | + |
| 9 | − |

Note:
++ indicates good growth, which means the medium is very turbid with visible bacterial pellets.
+ indicates a little growth, which means the medium is slightly turbid with a few visible bacterial pellets.
− indicates no growth, which means the fermentation broth is transparent without bacterial pellets.

Example 6

Tolerance Test of *Lactobacillus rhamnosus* CCFM1107 to pH

Hydrochloric acid of 1M is added to the MRS medium to adjust final pH at 1.5, 2.0, 2.5, 3.0, 3.5, 4.0 and 6.2 respectively. After sterilization, the *Lactobacillus rhamnosus* CCFM1107 of this invention is inoculated in the MRS medium by 5% (v/v). The growth of all groups is observed and the $OD_{600}$ value is measured after incubation at 37° C. for 24 h. The results are shown in Table 4 below.

The normal pH value of human gastric juice is 1.5-4.5, which fluctuates due to individual's diet composition. Generally, the pH value of gastric juice is about 3.0. To reach the intestine, the strains must have some acid resistance. As shown in Table 4 the *Lactobacillus rhamnosus* CCFM1107 of this invention can grow when the pH value is 3.0, which means the strains still have strong survival capacity at low pH.

TABLE 4

The growth of *Lactobacillus rhamnosus* CCFM1107 in MRS medium of different pH values

| pH value | CCFM1107 Growth | CCFM0528 Growth |
|---|---|---|
| 1.5 | − | − |
| 2.0 | − | − |
| 2.5 | − | − |
| 3.0 | + | − |
| 3.5 | ++ | + |
| 4.0 | ++ | ++ |
| 6.2 | ++ | ++ |

Note:
++ indicates good growth, which means the medium is very turbid with visible bacterial pellets.
+ indicates a little growth, which means the medium is slightly turbid with a few visible bacterial pellets.
− indicates no growth, which means the fermentation medium is clear and transparent without bacterial pellets.

Example 7

The Animal Experiments of *Lactobacillus rhamnosus* CCFM1107 Relieving Chronic Alcoholic Liver Injury To analyze the effectiveness of *Lactobacillus rhamnosus* CCFM1107 on alleviating alcoholic liver injury in this invention, mice were intragastrically administered with probiotics in a model of chronic alcoholic liver injury, which was established according to F. Sun and M. L. Xie, et al (Inhibitory effect of osthole on alcohol-induced fatty liver in mice. Digestive and Liver Disease, 2009, 41: 127-133).

Fifty male Kunming mice with the weight of 18±2 g were purchased from Shanghai Laboratory Animal Center (Shanghai, China). Animal license number is SCXK (Shanghai) 2007-0005.

Mice were fed with standard diet and housed in the clean grade animal laboratory of Medical College of Jiangnan University, at temperature of 20-23° C., a relative humidity of 50%-60%. Drinking water was provided ad libitum.

After acclimated for 3 days, the mice were randomly divided into five groups as shown in Table 5. Groups of 5-10 mice were treated according to the protocols illustrated in Table 5: twice gavages a day with alcohol in the morning and medication or probiotics of this invention in the afternoon.

TABLE 5

The animal experiment of *Lactobacillus rhamnosus* CCFM1107 relieving chronic alcoholic liver injury

| Groups | Feeding mode |
|---|---|
| Blank group | skim milk (am) + skim milk (pm) |
| Model group | alcohol (am) + skim milk (pm) |
| Drug group | alcohol (am) + liver-protecting tablet (pm) |
| Intervention group | alcohol (am) + CCFM1107 (pm) |
| Control group | alcohol (am) + N-9 (pm) |

Note:
am means in the morning and pm means in the afternoon; CCFM1107 refers to the *Lactobacillus rhamnosus* CCFM1107 of the present invention with high anti-oxidative capacity; and N-9 is a *Lactobacillus plantarum* with low anti-oxidative capacity as negative control.

The intragastric alcohol concentration is gradually increased by 20%-25%-30%-35%-40%, and maintained until the experiment ends since increased to 40% (v/v) within two weeks;

Sunflower Liver-aid Tablet (Heilongjiang Sunflower Pharmaceutical Co., Ltd.), which is a traditional Chinese herbs preparation, is used as the positive control for intragastric administration. Probiotic *Lactobacillus rhamnosus* CCFM1107 of this invention is used as concentrated freeze-dried powder, and incubated in a 37° C. water bath for 30 min at the concentration of $10^9$ cfu/mL before intragastric administration. All samples were administered to the mice by 10 mL/kgBW for 3 months. Mice were fasting for 24 hours after the last intragastric administration. Then mice were sacrificed and blood, liver and fecal samples were immediately collected to determine the levels of AST (aspartate aminotransferase), ALT (alanine aminotransferase), TG (triglycerides) and TC (total cholesterol).

AST, ALT, TG and TC assay kits were provided by Changchun Huili Biotech Co., Ltd., and MDA (malondialdehyde), GSH (glutathione), SOD (superoxide dismutase) and GSH-PX (glutathion peroxidase) assay kits were provided by Nanjing Jiancheng Bioengineering Institute. These results are shown in Table 6 to Table 13 and all data are analyzed using SPSS statistical software (Version 16.0). All results are expressed as the mean±SEM and the difference between groups are compared by One-way ANOVA.

The liver index is the ratio of liver weight to body weight, which reflects the health status of liver to some extent. Lesions of liver often cause atrophy or swelling of organs, which in turn affect the liver index. In this embodiment, mice liver indices of the five groups are shown in Table 6: the liver index of the model group is higher than that of the blank group with significant difference. After treatment, the liver indices of drug group and intervention group *Lactobacillus rhamnosus* CCFM1107 decline, and there are significant differences between the drug group and model group.

TABLE 6

The effect of *Lactobacillus rhamnosus* CCFM1107 on mice liver index (mean ± SEM, n = 10)

| Groups | Liver index (%) |
|---|---|
| Blank group | 2.98 ± 0.47 |
| Model group | 3.74 ± 0.52[a] |
| Drug group | 3.11 ± 0.39[b] |
| Intervention group | 3.31 ± 0.47 |
| Control group | 3.59 ± 0.36[a] |

Note:
[a]$p < 0.05$ compared with the blank group;
[b]$p < 0.05$ compared with the model group.

Alanine aminotransferase (ALT) and aspartate aminotransferase (AST) are mainly present in the cytoplasm of hepatocytes. The intracellular aminotransferase can enter into the blood to cause higher serum ALT and AST levels if the liver is damaged. AST is also distributed into mitochondria. The AST in mitochondrias will be released into the blood when the liver is severely damaged, elevating the serum AST level. Therefore the serum ALT and AST activities are the most sensitive biomarkers for ethanol-induced liver injury.

Table 7 shows that alcohol significantly increased the serum ALT and AST levels, and the drug and *Lactobacillus* rhamnosus CCFM1107 can reduce the ALT and AST levels in the drug group and intervention group, which are similar to those of the blank group.

TABLE 7

The effect of *Lactobacillus rhamnosus* CCFM1107 on transaminase activity (mean ± SEM, n = 10)

| Groups | AST(U/L) | ALT(U/L) |
|---|---|---|
| Blank group | 41.65 ± 10.02 | 27.49 ± 6.45 |
| Model group | 73.99 ± 7.89$^a$ | 36.03 ± 7.36$^a$ |
| Drug group | 43.92 ± 9.32$^b$ | 25.25 ± 3.01$^b$ |
| Intervention group | 47.88 ± 8.24$^b$ | 26.49 ± 5.29$^b$ |
| Control group | 74.80 ± 11.14$^a$ | 37.51 ± 8.84$^a$ |

Note:
$^a$P < 0.05 compared with the blank group;
$^b$P < 0.05 compared with the model group.

The steatosis and fat vacuole formation are also indicators of alcohol-induced liver injury, so the corresponding fat level in the blood can be measured to determine the injury degree. These results are shown in Table 8 below. Compared to the control group, the lipid level in model group is significantly increased, while the drug control treatment and *Lactobacillus rhamnosus* CCFM1107 can reduce the fat levels of the drug group and intervention group to the normal level.

TABLE 8

The effect of *Lactobacillus rhamnosus* CCFM1107 on blood lipid levels of mice (mean ± SEM, n = 10)

| Groups | Triglyceride (mmol/L) | Cholesterol (mmol/L) |
|---|---|---|
| Blank group | 2.24 ± 0.49 | 2.33 ± 0.51 |
| Model group | 3.74 ± 0.65$^a$ | 3.83 ± 0.61$^a$ |
| Drug group | 2.17 ± 0.45$^b$ | 2.49 ± 0.65$^b$ |
| Intervention group | 2.32 ± 0.63$^b$ | 2.80 ± 0.59$^b$ |
| Control group | 3.37 ± 0.72$^a$ | 3.80 ± 0.72$^a$ |

Note:
$^a$P < 0.05 compared with the blank group;
$^b$P < 0.05 compared with the model group.

Free radicals and lipid peroxidation is one of the important factors to cause damage to liver tissues. Malondialdehyde (MDA) is the product of lipid peroxidation. Thus, the amount of MDA reflects the degree of lipid peroxidation in vivo and indirectly reflects the degree of hepatocyte injury. The glutathione peroxidase (GSH-PX) using glutathione (GSH) as substrate can function with superoxide dismutase (SOD) to remove the reactive oxygen species, and suppress the oxidation of reactive oxygen species. Table 9 and table 10 show that alcohol can significantly decrease the GSH, GSH-PX and SOD levels, while the MDA concentration is increased correspondingly. However, treatment with drug or *Lactobacillus rhamnosus* CCFM1107 can elevate the GSH, GSH-PX and SOD levels, and reduce the MDA level. The effect of *Lactobacillus rhamnosus* CCFM1107 is even better than that of drug control group as the GSH concentration of the intervention group is higher than the normal levels, and the two enzyme indicators, glutathione peroxidase (GSH-PX) and superoxide dismutase (SOD), are also significantly improved in the intervention group (P<0.05).

TABLE 9

The effect of *Lactobacillus rhamnosus* CCFM1107 on mice MDA and GSH levels in liver homogenate(mean ± SEM, n = 10)

| Groups | MDA (nmol/mg protein) | GSH (mg/g protein) |
|---|---|---|
| Blank group | 6.01 ± 1.74 | 9.06 ± 2.41 |
| Model group | 12.92 ± 2.91$^a$ | 5.75 ± 1.67$^a$ |
| Drug group | 7.33 ± 2.05$^b$ | 6.99 ± 1.92 |
| Intervention group | 6.48 ± 2.28$^b$ | 9.85 ± 2.17$^b$ |
| Control group | 11.16 ± 2.77$^a$ | 6.11 ± 2.41$^a$ |

Note:
$^a$P < 0.05 compared with the blank group;
$^b$P < 0.05 compared with the model group.

TABLE 10

The effect of *Lactobacillus rhamnosus* CCFM1107 on mice SOD and GSH-PX levels in liver homogenate(mean ± SEM, n = 10)

| Groups | SOD(U/mgprot) | GSH-PX(Activity Unit) |
|---|---|---|
| Blank group | 105.22 ± 20.97 | 214.37 ± 23.79 |
| Model group | 71.88 ± 12.43$^a$ | 176.32 ± 19.24$^a$ |
| Drug group | 92.66 ± 14.52$^b$ | 179.01 ± 16.03$^a$ |
| Intervention group | 97.22 ± 13.84$^b$ | 203.14 ± 24.36 |
| Control group | 68.58 ± 15.17$^a$ | 205.55 ± 18.17$^b$ |

Note:
$^a$P < 0.05 compared with the blank group;
$^b$P < 0.05 compared with the model group.

Table 11 shows that alcohol intake not only increases the blood lipid level, but also increases the alcohol concentration in the liver, while treatment with the drug and *Lactobacillus rhamnosus* CCFM1107 significantly reduce the triglyceride and cholesterol levels in the liver homogenate. Besides, *Lactobacillus rhamnosus* CCFM1107 has the potency on reducing the triglyceride level, and the cholesterol-reducing effect of CCFM1107 is better in the drug group.

TABLE 11

The effect of *Lactobacillus rhamnosus* CCFM1107 on mice triglyceride and cholesterol levels in liver homogenate(mean ± SEM, n = 10)

| Groups | Triglyceride (mmol/L) | Cholesterol (mmol/L) |
|---|---|---|
| Blank group | 0.83 ± 0.09 | 1.34 ± 0.12 |
| Model group | 1.28 ± 0.23$^a$ | 2.26 ± 0.27$^a$ |
| Drug group | 0.99 ± 0.13$^b$ | 1.53 ± 0.21$^b$ |
| Intervention group | 0.88 ± 0.13$^b$ | 1.80 ± 0.26$^{a,b}$ |
| Control group | 1.23 ± 0.17$^a$ | 2.25 ± 0.33$^a$ |

Note:
$^a$P < 0.05 compared with the blank group;
$^b$P < 0.05 compared with the model group.

One of the major physiological functions of probiotics is to regulate intestinal microflora. Liver damage will inevitably lead to changes of intestinal microflora and probiotics play a vital role in maintaining the balance of intestinal micro-ecological environment. Feces from the intestine were collected in a sterilized tube, weighed, and diluted properly with sterilized buffer (1 L of PBS buffer containing 0.5 g of cysteine hydrochloride, 0.5 ml of Tween-80 and 0.5 g of agar, pH 7.4-7.6). 100 µl of diluted samples with appropriate dilutions is spread on different selective culture media to enumerate different bacteria, with modified MC medium for lactobacilli (Qingdao Hope Biotechnology Co., Ltd.), selective TPY medium for bifidobacteria (Qingdao Hope Biotechnology Co., Ltd.), VRBDA medium for Enterobacteria (Qingdao Hope Biotechnology Co., Ltd.), and EC medium for Enterococci (Qingdao Hope Biotechnology Co., Ltd.). Wherein *Lactobacillus* and *Bifidobacterium* enumeration were performed under anaerobic conditions at 37° C., Enterobacterium enumeration was performed under aerobic conditions at 37° C., and *Enterococcus* enumeration was performed under aerobic conditions at 42° C. The bacterial colonies were counted corresponding to 1 g of fecal sample after 48 h of incubation, and the result is expressed as log 10 (cfu/g intestinal feces). The serum endotoxin level is analyzed by enzyme-linked immunosorbent assay, and is examined in accordance with the manufacturer's instructions (Cusabio Co., Ltd.). The results are shown in Table 12 and Table 13.

TABLE 12

The effect of *Lactobacillus rhamnosus* CCFM1107 on intestinal microflora of mice (mean ± SEM, n = 10)

| Groups | Enterococcus | Enterobacterium | Lactobacillus | Bifidobacterium |
| --- | --- | --- | --- | --- |
| Blank group | 6.10 ± 0.17 | 6.13 ± 0.17 | 8.53 ± 0.20 | 9.35 ± 0.15 |
| Model group | 6.51 ± 0.23 | 7.59 ± 0.20$^a$ | 7.90 ± 0.21 | 8.14 ± 0.26$^a$ |
| Drug group | 6.30 ± 0.19 | 7.03 ± 0.24$^{a,b}$ | 8.06 ± 0.27 | 8.32 ± 0.17$^a$ |
| Intervention group | 4.48 ± 0.26$^{a,b}$ | 4.52 ± 0.20$^{a,b}$ | 8.99 ± 0.28$^b$ | 9.89 ± 0.16$^{a,b}$ |
| Control group | 5.54 ± 0.20$^b$ | 5.32 ± 0.13$^{a,b}$ | 8.72 ± 0.22$^b$ | 9.17 ± 0.21$^b$ |

Note:
$^a$P < 0.05 compared with the blank group;
$^b$P < 0.05 compared with the model group.

TABLE 13

The effect of *Lactobacillus rhamnosus* CCFM1107 on serum endotoxin level of mice (x ± s, n = 10)

| Groups | Serum endotoxin level (pg/mL) |
| --- | --- |
| Blank group | 28.29 ± 6.48 |
| Model group | 66.14 ± 12.47$^a$ |
| Drug group | 54.35 ± 13.24$^a$ |
| Intervention group | 27.93 ± 12.77$^b$ |
| Control group | 36.28 ± 13.12$^b$ |

Note:
$^a$P < 0.05 compared with the blank group;
$^b$P < 0.05 compared with the model group.

Table 12 and 13 show the number of enterobacteria obviously increases in the alcohol group, while those of lactobacilli and bifidobacteria greatly reduces, compared with the blank group. The number of lactobacilli and bifidobacteria in either the intervention group or the control group of probiotics group is far higher than those of the alcohol group. The *Lactobacillus rhamnosus* CCFM1107 group is even higher than the normal level, with a significant decrease in the number of enterococci and enterobacteria. However, the drug group has a little impact on the intestinal microflora, which are almost equivalent to the model group. Accordingly, the serum endotoxin levels in the model group and the drug group are higher than that in the blank group with significant difference (P<0.05). Probiotics treatment can reduce the endotoxin level significantly, so the serum endotoxin level in the *Lactobacillus rhamnosus* CCFM1107-treated group is slightly lower than that in the blank group.

Figure 4:
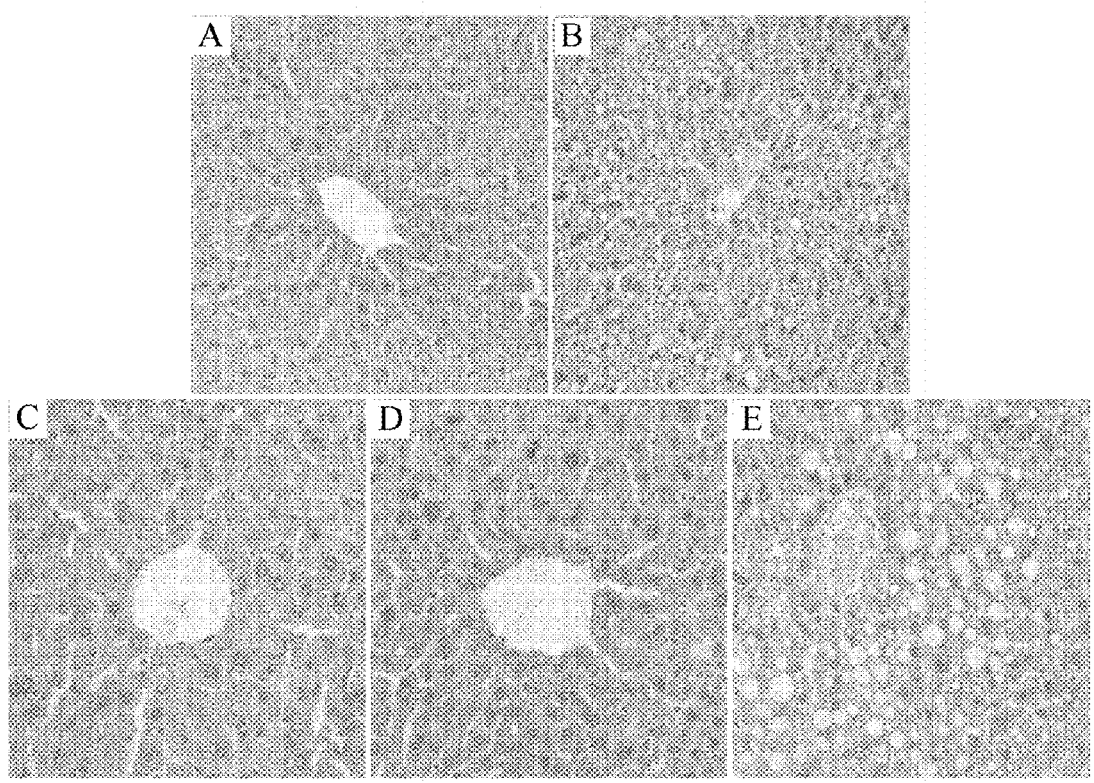
FIG. 4 shows HE staining morphological observation of pathological sections of mice liver in different groups (200×) A control group, B model group, C drug group, D CCFM1107 group, and E Lactobacillus plantarum N-9 group as negative control.
Figure 5:
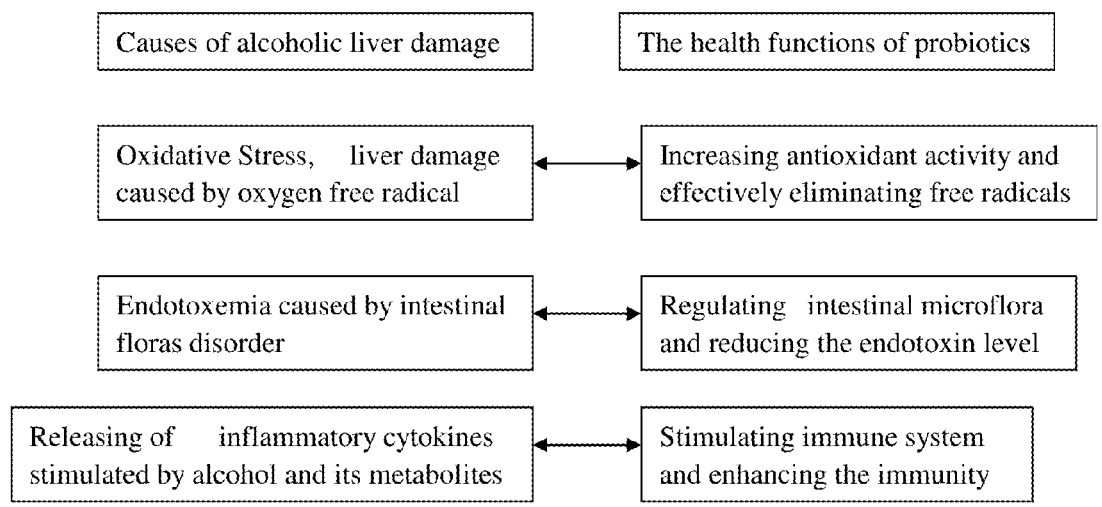
FIG. 5 shows the relationship between causes of the alcoholic liver injury and probiotic health effects.
Figure 6:
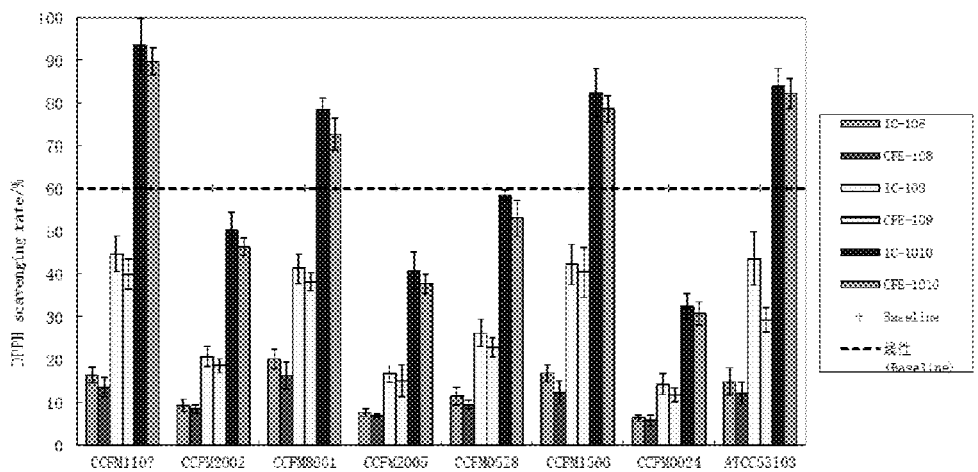
FIG. 6 Scavenging of DPPH free radicals by intact cells and free-cell extracts of LAB.

The samples at the same part of liver in all groups are taken to evaluate the effect of probiotics in relieving alcoholic liver injury. The mice pathological sections HE (hematoxylin-eosin) staining are shown in FIG. 4. Blank group (FIG. 4A): complete hepatic cords with radial pattern, clear liver lobules, distinct boundaries and uniform cytoplasm of liver cell, no fatty cavity or inflammatory infiltration; model group (FIG. 4B): obvious steatosis, large area of fatty cavities, swelling and deformed liver cells with turbid cytoplasm and network structure, slight karyopyknosis and inflammatory cell infiltration; drug group (FIG. 4C): compared with the model group, this group has better conditions: nearly no fat bubbles, slight inflammatory cell infiltration, and slight karyopyknosis; CCFM1107 intervention group (FIG. 4D): hepatic lobule with clear boundaries, neatly arranged and normal liver cells; and negative control group of *Lactobacillus plantarum* N-9 strain group (FIG. 4E): more fat cavities, swelling liver cells, mesh structure and slight inflammatory infiltration.

In conclusion, the *Lactobacillus rhamnosus* CCFM1107 can reduce the serum transaminase activity and lipid level, improve the antioxidative capacity of mice, inhibit free radicals formation, regulate intestinal microflora, lower the serum endotoxin level, and prevent alcohol-induced steatosis in the mice models of chronic alcoholic-induced liver injury. The biological indices of serum and liver show that the *Lactobacillus rhamnosus* CCFM1107 of this invention has good physiological effects on relieving chronic alcoholic-induced liver injury and can be further used for developing functional foods or drugs, as well as their compositions.

Application Example 1: Preparation of Cow Milk Containing CCFM1107 with *Lactobacillus rhamnosus* CCFM1107

Firstly, the starter culture containing *Lactobacillus rhamnosus* CCFM1107 is prepared by the following steps:

The original *Lactobacillus rhamnosus* CCFM1107 by 12% weight of skim milk are inoculated in the skim milk which is sterilized with the 145C type sterilizer of UK SPX APV at 110° C. for 10 min, and then cultured at 37° C. for 14 h into the curd. The curd is cultured and activated for two subsequent generations at the same conditions to obtain the fermented skim milk as mother starter.

The mother starter by 5% volume of skim milk is inoculated in the skim milk which is sterilized with the 145C sterilizer at 110° C. for 10 min, and then incubated at 37° C. for 14 h to obtain the starter culture with the viable bacteria concentration of 3×10$^9$ cfu/mL.

The raw cow milk is sterilized at 95° C. for 20 min with the said sterilizer, cooled to 4° C., then added with the starter culture containing *Lactobacillus rhamnosus* CCFM1107 to obtain the medium with the concentration over 10$^6$ cfu/mL, and refrigerated at 4° C. to obtain the cow milk containing *Lactobacillus rhamnosus* CCFM1107.

Application Example 2: Preparation of Milk Powder with Lactobacillus rhamnosus CCFM1107

Firstly, the starter culture containing Lactobacillus rhamnosus CCFM1107 is prepared by the following steps:

The Lactobacillus rhamnosus CCFM1107 by 5% weight of skim milk MRS medium are inoculated in the MRS liquid medium, cultured at 37° C. for 12 h, and then cultured and activated for two subsequent generations at the same conditions.

The activated culture are inoculated in MRS medium by 4% volume of MRS liquid medium, cultured at 37° C. for 16 h, and then centrifuged at the speed of 4000 r/min at 4° C. for 15 min to obtain the cell pellets after removing supernatant. The cell pellets are suspended with sterilized skim milk to obtain the starter culture with the viable bacteria concentration of $1 \times 10^9$ cfu/mL.

The raw milk is sterilized at 140° C. for 2 s with the PT-20C-R tube-plate type UHT sterilizer of Japanese Powerpoint International, then cooled to 37° C., inoculated with the starter culture containing Lactobacillus rhamnosus CCFM1107 of this invention by 4% volume of the raw milk, and fermented at 37° C. for 16 h to obtain the fermented milk containing Lactobacillus rhamnosus CCFM1107. The fermented milk containing Lactobacillus rhamnosus CCFM1107 is added to the sterilized raw milk by volume ratio of 1:3, homogenized with a high-pressure homogenizer of Shanghai Donghua High-pressure Homogenizer Factory GYB40-10S; vacuum concentrated with a vacuum evaporator of Yangzhou Food Machinery Factory, and then spray dried with an experimental spray dryer of Shanghai Triowin Technology Co., Ltd. to obtain the milk powder containing Lactobacillus rhamnosus CCFM1107.

Application Example 3: Preparation of Milk Capsules with Lactobacillus rhamnosus CCFM1107

Firstly, the starter culture containing Lactobacillus rhamnosus CCFM1107 is prepared by the following steps:

The original Lactobacillus rhamnosus CCFM1107 by 3% weight of skim milk MRS medium are inoculated in the MRS liquid medium, cultured at 37° C. for 16 h, and then cultured and activated for two subsequent generations at the same conditions.

The activated culture by 2% volume of MRS liquid medium are inoculated in MRS liquid medium, cultured at 37° C. for 18 h, and then centrifuged at the speed of 4000 r/min at 4° C. for 15 min to obtain the cell pellets after removing supernatant. The cell pellets are suspended with sterilized skim milk to obtain the starter culture with the viable bacteria concentration of $2 \times 10^9$ cfu/mL.

The raw milk is sterilized at 140° C. for 2 s with the PT-20C-R tube-plate type UHT sterilizer of Japanese Powerpoint International, then cooled to 37° C., inoculated with the starter culture containing Lactobacillus rhamnosus CCFM1107 of this invention by 4% volume of the raw milk, and fermented at 37° C. for 16 h to obtain the fermented milk containing Lactobacillus rhamnosus CCFM1107. The fermented milk containing Lactobacillus rhamnosus CCFM1107 is added to the sterilized raw milk by volume ratio of 1:3, homogenized with a high-pressure homogenizer of Shanghai Donghua High-pressure Homogenizer Factory GYB40-10S; vacuum concentrated with a vacuum evaporator of Yangzhou Food Machinery Factory, and then spray dried with an experimental spray dryer of Shanghai Triowin Technology Co., Ltd. to obtain the milk powder. The milk powder is filled into capsules to obtain the capsule products.

Application Example 4: Preparation of Fermented Milk with Lactobacillus rhamnosus CCFM1107

Firstly, the starter culture containing Lactobacillus rhamnosus CCFM1107 is prepared by the following steps:

The original Lactobacillus rhamnosus CCFM1107 by 12% weight of skim milk are inoculated in the skim milk which is sterilized with the 145C type sterilizer of UK SPX APV at 110° C. for 10 min, and then cultured at 37° C. for 16 h into the curd. The curd is cultured and activated for two subsequent generations at the same conditions to obtain the fermented skim milk as mother starter;

The mother starter culture by 3% volume of sterilized milk is inoculated in the skim milk which is sterilized with the 145C type sterilizer at 110° C. for 10 min, and then cultured at 37° C. for 16 h to obtain the curd as starter culture with the viable bacteria concentration of $1 \times 10^9$ cfu/m L.

The raw milk is sterilized at 95° C. for 20 min with the 145C type sterilizer of UK SPX APV, cooled to 37° C., then added with the starter culture containing Lactobacillus rhamnosus CCFM1107 by 4% volume of the raw milk and Lactobacillus bulgaricus and Streptococcus thermophilus that can prepare fermented milk by 4% volume of the raw milk, fermented at 37° C. to 0.6% titration acidity (by lactic acid), cooled to 4° C. and stored at the refrigerating temperature to obtain the fermented milk.

The invention claimed is:

1. A method for preparing a dairy composition, which comprises: i) inoculating sterilized skim milk with Lactobacillus rhamnosus, and incubating at 37° C. for 14-16 h, which forms as curd; ii) inoculating sterilized skim milk with the curd of step i), and incubating at 37° C. for 14-16 h, which results in curd; iii) inoculating sterilized skim milk with the curd of step ii), and incubating at 37° C. for 14-16 h, which forms curd that named as a mother starter; iv) inoculating sterilized skim milk with the mother starter, and incubating at 37° C. for 14-16 h, which forms curd as a starter culture which contains $1-3 \times 10^9$ CFU/ml bacteria; v) mixing the starter culture with a sterilized raw milk which contains at least $10^6$ CFU/ml Lactobacillus rhamnosus, and storing at a refrigerator, characterized in that the Lactobacillus rhamnosus is Lactobacillus rhamnosus CCFM1107, deposited at the General Microbiology Culture Collection Center of China Committee for Culture Collection of Microorganisms under accession number CGMCC5496.

2. The method according to claim 1, which further comprises: a) mixing the raw milk with the starter culture, incubating at 37° C. for 12-18 h which yields fermented milk after the step iv) of claim 1; then b) mixing the fermented milk and the sterilized raw milk, homogenizing, vacuum-concentrating and spray-drying which yields milk powders which are optionally capsulated as milk capsules.

3. The method according to claim 1, wherein the raw milk is one or more kinds of milk selected from skim milk, fresh milk, or reconstituted milk wherein the milk is selected from cow's milk, goat's milk or mare's milk.

4. The method according to claim 1, which further comprises: c) adding 3-5% of the starter culture and 3-5% of commercial culture by volume into the sterilized raw milk after the step iv) of claim 1; and chi) homogenizing, fermenting at 37° C. until the concentration of lactic acid is up 0.6-0.7%; iii) cooling and storing in a refrigerator.

5. The method according to claim 4, wherein the commercial culture contains Lactobacillus bulgaricus or/and Streptococcus thermophilus.

* * * * *